(12) United States Patent  
Suzuki et al.

(10) Patent No.: US 8,972,044 B2  
(45) Date of Patent: Mar. 3, 2015

(54) AUTOMATED SAMPLE TEST SYSTEM, AND METHOD FOR CONTROLLING SAME

(75) Inventors: Atsushi Suzuki, Naka (JP); Koji Kamoshida, Hitachinaka (JP); Masashi Akutsu, Hitachinaka (JP); Kenichi Takahashi, Naka (JP); Hiroshi Ohga, Hitachiomiya (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/816,897

(22) PCT Filed: Sep. 15, 2011

(86) PCT No.: PCT/JP2011/071129  
§ 371 (c)(1),  
(2), (4) Date: Mar. 1, 2013

(87) PCT Pub. No.: WO2012/043261  
PCT Pub. Date: Apr. 5, 2012

(65) Prior Publication Data  
US 2013/0197690 A1    Aug. 1, 2013

(30) Foreign Application Priority Data  
Sep. 28, 2010 (JP) .................................. 2010-216325

(51) Int. Cl.  
*G06F 7/00* (2006.01)  
*G01N 35/04* (2006.01)  
(Continued)

(52) U.S. Cl.  
CPC ............ *G01N 35/04* (2013.01); *G01N 35/0092* (2013.01); *G01N 35/026* (2013.01); *G01N 2035/0094* (2013.01)  
USPC .............. 700/216; 700/218; 700/83; 422/65; 422/63; 422/64; 436/47; 436/174

(58) Field of Classification Search  
USPC ........................................................ 700/216  
See application file for complete search history.

(56) References Cited

U.S. PATENT DOCUMENTS 5,380,488 A * 1/1995 Wakatake ........................ 422/65  
6,442,440 B1 * 8/2002 Miller ............................. 700/83  
(Continued)

FOREIGN PATENT DOCUMENTS

JP        02-306165 A     12/1990  
JP        08-122337 A      5/1996  
(Continued)

OTHER PUBLICATIONS

International Preliminary Report on Patentability received in International Application No. PCT/JP2011/071129 dated Apr. 25, 2013.

*Primary Examiner* — Gene Crawford  
*Assistant Examiner* — Kyle Logan  
(74) *Attorney, Agent, or Firm* — Mattingly & Malur, PC (57) ABSTRACT

A method for controlling an automated sample test system includes a samples conveyance line for conveying samples racks, each holding samples, to a plurality of processing units, and an empty-rack stock section in which to stock samples racks not holding a sample. The control method is designed to collect information on whether the processing units are in need of a supply of empty samples racks, and then supply empty samples racks from the empty-rack stock section to the processing units based on the information. Decreases in throughput can be prevented by leveling the number of empty samples racks supplied to the processing units that require empty samples racks.

11 Claims, 7 Drawing Sheets

(51) Int. Cl.
*G01N 35/00* (2006.01)
*G01N 35/02* (2006.01)

(56) References Cited

U.S. PATENT DOCUMENTS

| | | | |
|---|---|---|---|
| 6,599,749 B1 * | 7/2003 | Kodama et al. | 436/47 |
| 7,700,043 B2 * | 4/2010 | Mimura et al. | 422/65 |
| 7,842,237 B1 * | 11/2010 | Shibuya et al. | 422/64 |
| 2002/0164269 A1 * | 11/2002 | Ngo et al. | 422/63 |
| 2008/0069730 A1 | 3/2008 | Itoh | |
| 2010/0166605 A1 * | 7/2010 | Hamada et al. | 422/65 |
| 2011/0076780 A1 * | 3/2011 | Yamato et al. | 436/174 |
| 2011/0160899 A1 * | 6/2011 | Tatsutani et al. | 700/218 |

FOREIGN PATENT DOCUMENTS

| | | |
|---|---|---|
| JP | 2001-141732 A | 5/2001 |
| JP | 2002-357612 A | 12/2002 |
| JP | 3618067 B2 | 2/2005 |
| JP | 2005-156196 A | 6/2005 |
| JP | 2007-309675 A | 11/2007 |
| JP | 4336360 B2 | 9/2009 |

\* cited by examiner

| | Information from processing unit to controller | | | | | | Instructions from controller to processing unit | | | | | |
|---|---|---|---|---|---|---|---|---|---|---|---|---|
| | Processing Unit | A | B | C | D | E | Processing Unit | A | B | C | D | E |
| State I (501) | Samples rack required | YES | NO | YES | NO | YES | Samples rack stopper instruction | — | — | — | — | OPEN |
| | | | | | | | Empty-rack convey line instruction | DRIVE | DRIVE | DRIVE | DRIVE | DRIVE |
| | | | | | | | Samples rack acquisition rate | 1:1 | — | 2:1 | — | 3:1 |
| State II (502) | Samples rack required | YES | NO | YES | NO | NO | Samples rack stopper instruction | — | — | — | — | OPEN |
| | | | | | | | Empty-rack convey line instruction | DRIVE | DRIVE | DRIVE | DRIVE | DRIVE |
| | | | | | | | Samples rack acquisition rate | 1:1 | — | 2:1 | — | — |
| State III (503) | Samples rack required | YES | NO | YES | NO | NO | Samples rack stopper instruction | — | — | — | — | OPEN |
| | | | | | | | Empty-rack convey line instruction | DRIVE | DRIVE | DRIVE | DRIVE | DRIVE |
| | | | | | | | Samples rack acquisition rate | 1:1 | — | 2:1 | — | — |
| State IV (504) | Samples rack required | NO | NO | YES | NO | NO | Samples rack stopper instruction | — | — | — | — | OPEN |
| | | | | | | | Empty-rack convey line instruction | DRIVE | DRIVE | DRIVE | DRIVE | DRIVE |
| | | | | | | | Samples rack acquisition rate | — | — | 1:1 | — | — |
| State V (505) | Samples rack required | NO | NO | NO | NO | NO | Samples rack stopper instruction | — | — | — | — | CLOSE |
| | | | | | | | Empty-rack convey line instruction | STOP | STOP | STOP | STOP | STOP |
| | | | | | | | Samples rack acquisition rate | — | — | — | — | — |

FIG.6

AUTOMATED SAMPLE TEST SYSTEM, AND METHOD FOR CONTROLLING SAME

TECHNICAL FIELD

The present invention relates generally to automated sample test systems, and more particularly, to an automated sample test system for processing clinical laboratory tests on a multitude of patient samples.

BACKGROUND ART

In recent years, many different types of automated apparatuses have been introduced in medical fields to save the labor associated with laboratory test operations. During the laboratory test operations in a hospital, inpatient and outpatient samples to be tested are collected in various sections of the hospital and then subjected to batch processing in a test room. Sample-specific laboratory test items are communicated from doctors to the test room through an online information-processing system. Conversely, test results are reported on-line from the test room to each doctor.

A large majority of test items on blood and urine require centrifugation, destoppering, dispensing/aliquoting, and other test preprocessing operations, and these operations account for a high percentage of the total testing time required.

Next, an operational flow of a general, automated sample test system is outlined below. Test tubes containing the blood and other body fluids which have been sampled from patients are placed in a samples rack and loaded into the system. The system then reads bar code information from labels attached to each loaded sample, and recognizes a type of the sample.

As mentioned above, there are such test preprocessing operations as centrifugation, destoppering, and dispensing/aliquoting (hereinafter, referred to simply as dispensing). The kind and/or details of preprocessing required, however, differ according to the type of test to be conducted. For example, centrifugation may not be required for urinary tests. When the sample test type requires centrifuging, then destoppering and dispensing follow the centrifuging operation. Dispensing is a process for creating child samples from a parent sample, and this process allows subdivided child samples to be simultaneously conveyed to, for example, a plurality of analyzers connected on-line to the system. The dispensing process also includes a function that, in order to conduct tests in offline analyzers not connected to the system, unloads onto a sorting tray the child samples to which is attached the same bar code as that of the parent sample. Samples that have gone through all processing steps are stored into a storage unit.

Automated sample test systems such as the one outlined above are usually introduced into medical facilities of a relatively large scale, and the fact is that hundreds to thousands of patient samples undergo processing in one day at these facilities. At the large-scale facilities, a plurality of samples are taken from one patient, for conducting biochemical tests, immunological tests, coagulation tests, and various other tests. Hence, the number of samples racks loaded into the automated sample test system has needed to match the above throughput, and a space for placing and storing these racks has also been required.

As described in Patent Document 1, for example, a conventional unit for loading samples racks into an automated sample test system is known to employ a scheme in which a large quantity of samples racks are set up in an apparatus in order to conduct appropriate processing according to the type of sample.

In addition, Patent Document 2 describes a scheme intended to reduce a placement area for a large quantity of samples racks by setting up these samples racks in certain numbers collectively on trays, then arranging each of these trays in multiple tiers for both a samples rack supply unit and a samples rack recovery unit, and supplying/recovering each samples rack by means of an elevator mechanism of a vertically driven type.

Patent Document 3 proposes a scheme for coupling an apparatus to an endlessly operating type of conveyance line and repeatedly routing samples racks to enable reuse of the racks.

Patent Document 4 introduces a scheme for arranging a plurality of conveyance lines near a loading unit, stocking samples racks on each of the conveyance lines, and repeatedly routing each of the samples racks for reuse.

PRIOR ART LITERATURE

Patent Documents

Patent Document 1: Japanese Patent No. 3618067
Patent Document 2: JP-2007-309675-A
Patent Document 3: JP-8-122337-A
Patent Document 4: Japanese Patent No. 4336360

SUMMARY OF THE INVENTION

Problems to be Solved by the Invention

The methods described in above Patent Documents 1 and 2 are intended to process a large quantity of samples, and both require providing a sufficient quantity of samples racks to accommodate samples to be tested, so these methods will inevitably make the system large in scale and complex. In addition, these methods have traditionally required an operator's trouble of replenishing the system with a large quantity of samples racks before using the system.

The method described in Patent Document 3, on the other hand, does not require a large quantity of samples racks since the system renders samples racks reuseable by circulating the samples rack conveyance lines in a loop inside the system. However, since empty samples racks and samples racks with samples placed therein pass through the same conveyance line, conveyance line congestion tends to occur, which makes it difficult to build a system high in throughput. Complexity of conveyance control would also be inevitable by reason of, for example, a need arising to discriminate empty samples racks from samples racks with samples placed therein.

One useable way to avoid the complexity of conveyance control would be by providing a dedicated conveyance line for empty samples racks separately from a samples rack conveyance line with samples placed thereupon. Even so, a decrease in throughput is likely since the conveyance lines will intersect with each other.

The method described in Patent Document 4 does not require a large quantity of samples racks, because the plurality of conveyance lines are arranged and empty samples racks are returned. If a processing unit requiring a samples rack exists in plurality, however, possible variations in a stock volume of empty samples racks between the processing units may cause difficulty in building a system having high throughput.

The present invention has been made keeping in mind the above problems associated with the prior art, and an object of the invention is to provide an automated sample test system designed so that a more highly extendible system suitable for faster processing and adapted to avoid complication of conveyance control as well as decreases in processing rate can be easily constructed without upsizing the system.

Means for Solving the Problems

In order to solve the foregoing problems, the automated sample test system according to the present invention features the following.

Specifically, there is provided a method for controlling the automated sample test system including a samples conveyance line for conveying samples racks, each holding samples, to a plurality of processing units, and an empty-rack stock section in which to stock samples racks not holding a sample. The control method includes: collecting information on whether the processing units are in need of a supply of empty samples racks, and supplying empty samples racks from the empty-rack stock section to the processing units in accordance with the information.

Effects of the Invention

In accordance with the present invention, an automated sample test system adapted to continuously supply and recover empty racks so as not to reduce processing capabilities, and having high enough extendibility to suit a particular scale of facilities, can be supplied without upsizing and complexifying the system.

MODE FOR CARRYING OUT THE INVENTION

Figure 1:
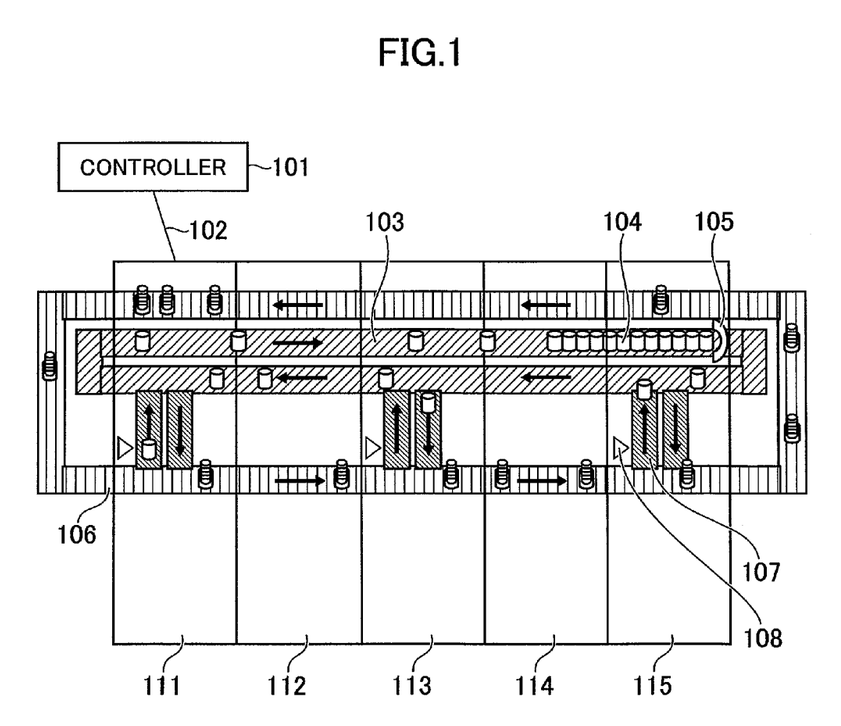
FIG. 1 is a schematic total block diagram showing a configuration of an automated sample test system according to an embodiment of the present invention, this system including a samples rack conveyance line section.

FIG. 1 is a schematic total block diagram showing a configuration of an automated sample test system according to an embodiment of the present invention, this system including a samples rack conveyance line section.

This automated sample test system includes an automatic analyzer that analyzes samples to be tested (e.g., biological samples of serum, urine, and the like, or liquid mixtures of these samples and reagents), by determining physical characteristics of each sample, or the system automatically executes necessary processing before the automatic analyzer conducts the analysis. The system also includes processing units that each executes one of various steps such as container destoppering, dispensing/aliquoting, container stoppering, stirring, and analysis.

Five processing units, A111 to E115, exist in the present embodiment. Of the five processing units, three units, namely A111, C113, E115, each need an empty samples rack to process loaded samples, and each include a connecting conveyance line 107 to load empty samples racks from a conveyance line 103 for empty racks. While the five units, A111 to E115, are only shown as processing units in FIG. 1, up to 10 units or more may be connected in large-scale facilities.

The conveyance line 103 for empty racks is disposed at a lower position than a main conveyance line 106, and the main conveyance line 106 and the conveyance line 103 for empty racks are interconnected using the connecting conveyance line 107. A way to connect the main conveyance line 106 and empty-rack conveyance line 103 of different installation heights above a floor level can be by either disposing the connecting conveyance line 107 in an inclined condition or using an elevator mechanism of a vertically driven type.

When a processing unit needs an empty samples rack 104, the processing unit acquires one empty samples rack 104 from the empty-rack conveyance line 103 and then conveys the acquired empty samples rack 104 to the main conveyance line 106 via the connecting conveyance line 107.

After the empty samples rack 104 has been conveyed to the main conveyance line 106, samples are placed in the empty samples rack 104 by a samples chuck mechanism not shown, and then during conveyance of the samples rack 104 by the main conveyance line 106, the processing unit processes the samples.

In addition, upon the samples chuck mechanism removing the samples from the samples rack 104 internally having held the samples up until that time, the emptied samples rack 104 is conveyed, via the connecting conveyance line 107, to the empty-rack conveyance line 103 located at a position lower than that of the connecting conveyance line 107. In the present embodiment, empty samples racks are held on the empty-rack conveyance line 103. The automated sample test system, however, can have any other holding structure, only if the hold structure enables empty racks to be stocked. For example, the holding structure may be such that empty samples racks are accommodated in grid-like array form and each conveyed sequentially to any processing units requiring an empty rack, or such that a rotatable disk with empty samples racks arranged circumferentially thereupon in advance rotates to accommodate/convey the empty samples racks.

The empty samples rack 104 that has been conveyed to the empty-rack conveyance line 103 is stocked at a predetermined position thereupon by a samples rack stopper 105. The samples rack stopper 105 is a mechanism for stemming and stopping a movement of the empty samples rack lying on the empty-rack conveyance line 103, and the stopper can shift its operation from a closed state to an open state, and vice versa, depending upon a command from a controller 101.

While FIG. 1 shows the configuration with one samples rack stopper 105 provided on the empty-rack conveyance line 103, a configuration with the samples rack stopper 105 in plurality or without the stopper may replace the shown configuration.

If a plurality of samples rack stoppers 105 are provided, even in a case that a large number of processing units are interconnected and a long conveyance line for empty racks is present, empty samples racks can be held evenly upon the conveyance line for empty racks. Thus, even if a route for conveying empty samples racks to the processing units requiring an empty samples rack is long, an empty samples rack can be supplied to each processing unit within a relatively short time.

Conversely if no samples rack stopper is provided, it becomes achievable, in spite of empty samples racks being scattered over the empty samples rack conveyance line, to evenly supply the empty samples racks by conveying each optionally according to rack distribution rules of the present invention. In this case, since no samples rack stopper is provided, apparatus costs can be reduced and the conveyance process for the empty samples racks can be simplified.

Figure 6:
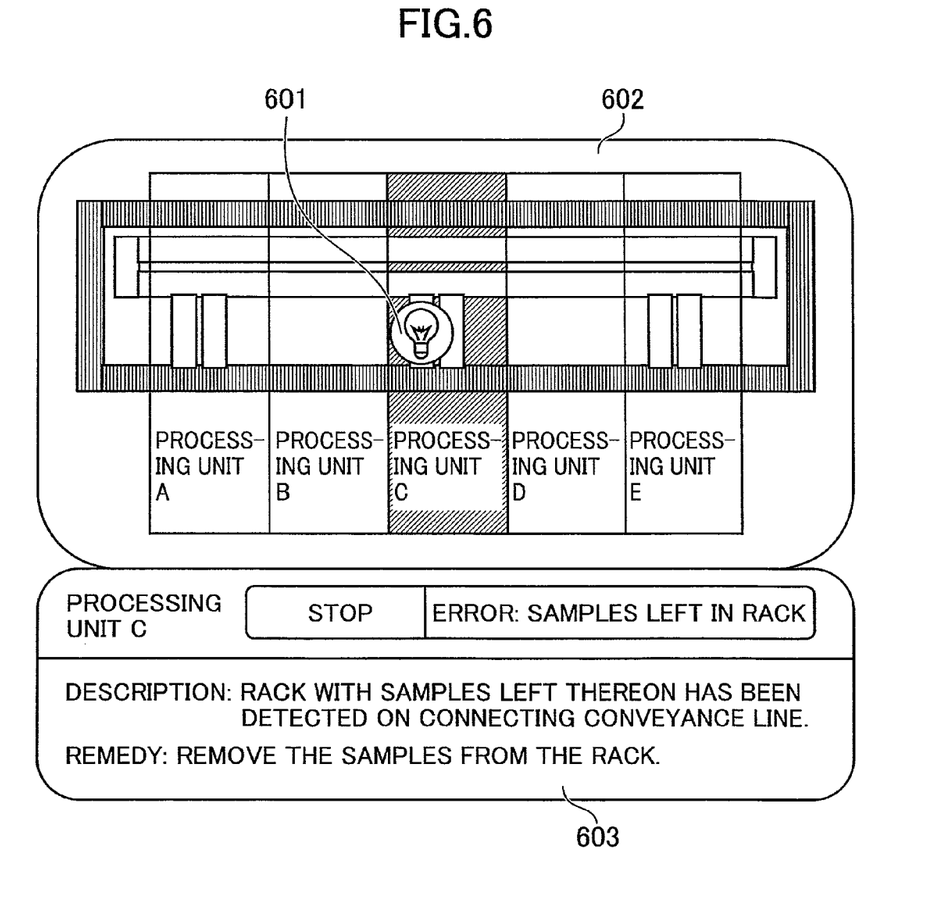
FIG. 6 shows an example of a screen displayed in the present invention to notify to an operator a passage of a samples rack with samples placed therein.

Additionally, for reasons such as a samples removal failure in the samples chuck mechanism or an artificial mistake in operations, an apparatus might make an attempt to erroneously draw a samples rack 104 with samples remaining placed therein, onto the empty-rack conveyance line 103, so a samples existence detection sensor 108 for detecting such may be provided on the connecting conveyance line 107. Upon detecting a passage of the samples rack with samples placed therein, the samples existence detection sensor 108 stops the connecting conveyance line 107 and prevents the samples from being accommodated on the empty-rack conveyance line 103. Alternatively, the system may notify the above to an operator and request him or her to remove the samples. One conceivable method of notifying the above event to the operator would be by providing the controller 101 with such a screen as in FIG. 6.

Figure 2:
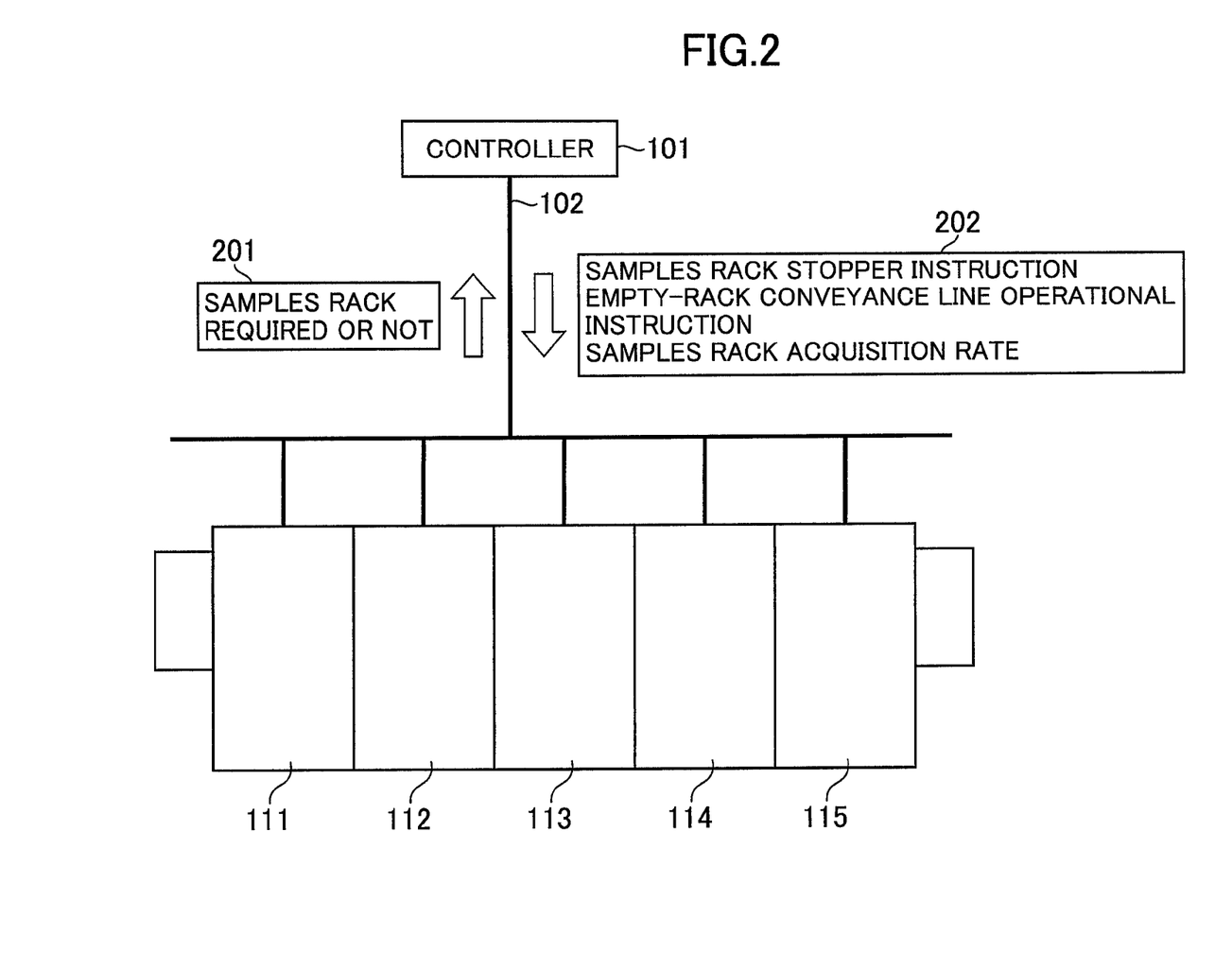
FIG. 2 shows information exchanged between a controller and processing units according to the present invention.

Information that is exchanged between the processing units and the controller according to the present invention is shown in FIG. 2.

The processing units A111 to E115 and the controller 101 are interconnected via a communication cable 102. The communication cable 102 may be replaced by communication means that enables wireless information exchange, or replaced by any other means, if the means enables the controller 101 to always or periodically receive information that indicates whether each processing unit is in need of supply of an empty samples rack.

The controller 101 receives the above information, then gives a samples rack stopper instruction relating to the opening/closing of the samples rack stopper 105 placed on the empty-rack conveyance line 103, an empty-rack conveyance line activation instruction indicating whether the empty-rack conveyance line 103 is to be driven, and specifies to individual processing units a samples rack acquisition rate which indicates, of all empty samples racks 104 that the empty-rack conveyance line 103 conveys, only empty samples racks 104 that each processing unit has been permitted to acquire.

Figure 3:
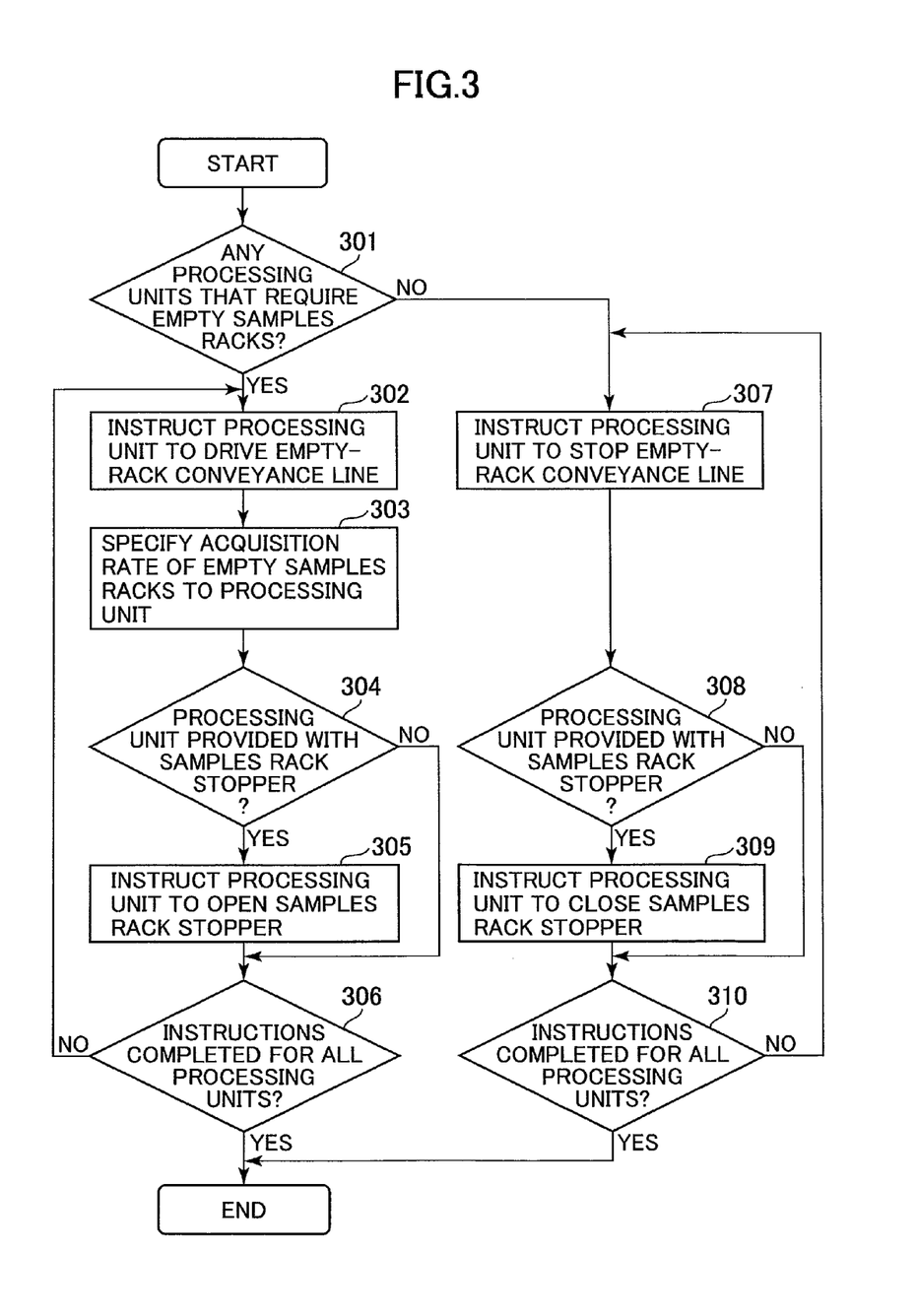
FIG. 3 shows a flow of process steps in which the controller in the present invention determines instructions to be given to the processing units.

A flow of process steps in which the controller 101 in the present invention determines the instructions to be given to the processing units is shown in FIG. 3. First, the controller 101 executes empty-rack supply determining step 301. In empty-rack supply determining step 301, the controller 101 determines whether either of the processing units connected to the empty-rack conveyance line via the connecting conveyance line is in need of an empty samples rack 104. If a processing unit in need of an empty samples rack 104 is present, the controller 101 next executes empty-rack conveyance line driving instruction step 302 to instruct all processing units to drive the empty-rack conveyance line 103.

The controller 101 further executes samples rack acquisition rate determining step 303 to specify, to the processing unit in need of an empty samples rack 104, a rate that indicates, of all empty racks that arrive, only those which the processing unit can acquire.

Furthermore, if the empty-rack conveyance line includes a samples rack stopper 105 and has a samples rack(s) stocked thereupon by means of the stopper, the controller 101 executes samples rack stopper opening instruction step 305 to instruct the processing unit to open the samples rack stopper 105.

If the process from empty-rack conveyance line driving instruction step 302 to samples rack stopper opening instruction step 305 is not yet completed for all processing units that have notified to the controller 101 the need of supply of an empty samples rack, process control is returned from end-of-instruction determining step 306 to empty-rack conveyance line driving instruction step 302.

Conversely if there is no processing unit in need of supply of an empty samples rack 104, the controller 101 executes empty-rack conveyance line deactivation instruction step 307 to instruct each processing unit to stop the driving of the empty-rack conveyance line 103. The execution of empty-rack conveyance line deactivation instruction step 307 prevents the driving of the empty-rack conveyance line from continuing, if an empty samples rack is not being exchanged.

If the processing unit is equipped with a samples rack stopper 105, the controller 101 executes samples rack stopper closing instruction step 309 to instruct the processing unit to close the samples rack stopper 105. If the instruction is unfinished for all processing units, process control is returned from end-of-instruction determining step 310 to empty-rack conveyance line deactivation instruction step 307.

Figure 4:
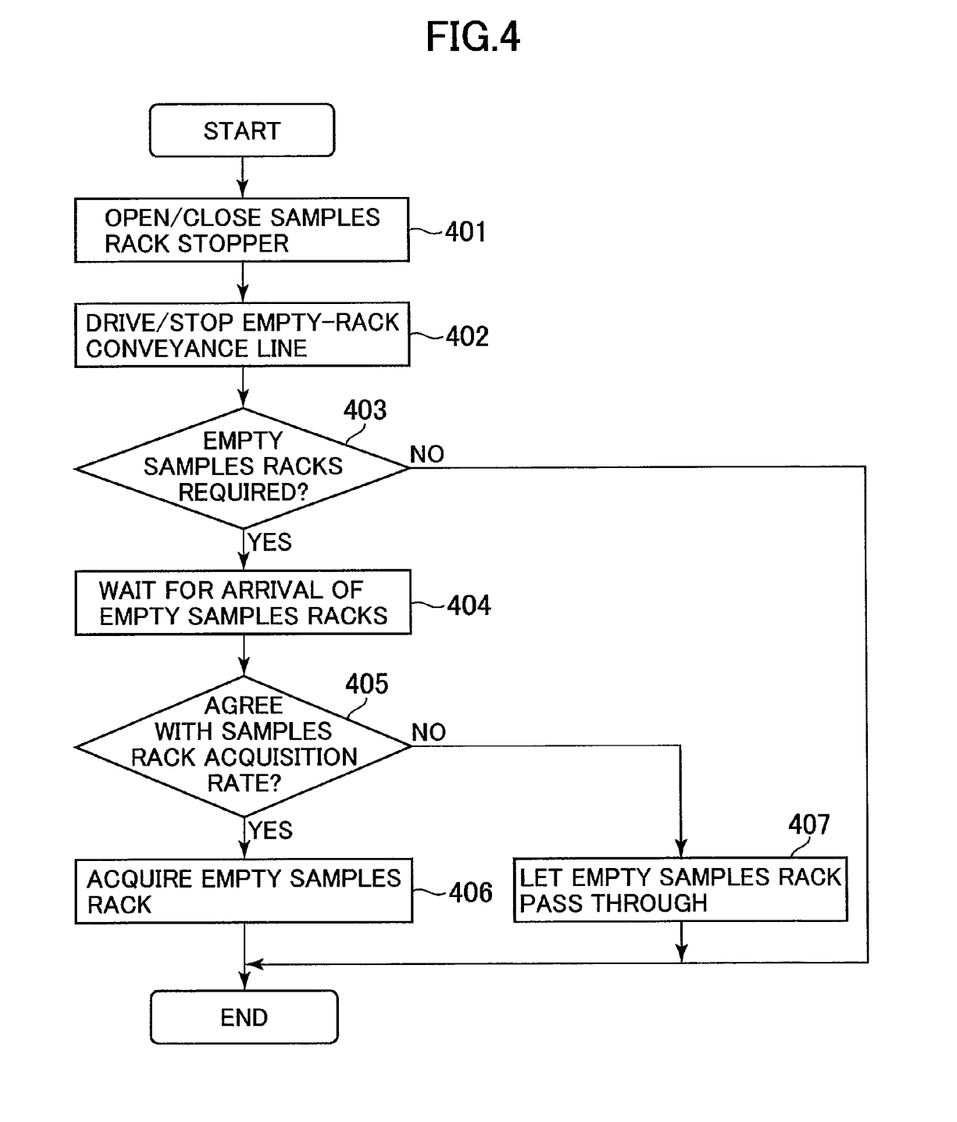
FIG. 4 shows a flow of process steps in which a processing unit in the present invention determines acquisition of an empty samples rack.

A flow of process steps in which a processing unit in the present invention determines the acquisition of an empty samples rack is shown in FIG. 4.

If the processing unit is equipped with a samples rack stopper, the controller 101 executes samples rack stopper opening/closing step 401 to open or close the samples rack stopper 105, depending upon the samples rack stopper instruction from the controller 101.

The controller 101 executes empty-rack conveyance line driving instruction step 402 to drive or stop the empty-rack conveyance line 103, depending upon the empty-rack conveyance line driving instruction.

In empty-rack arrival awaiting step 404, the processing unit requiring an empty samples rack waits for the empty samples rack 104 to arrive at the connecting conveyance line that will load it into that processing unit, and depending upon the samples rack acquisition rate specified from the controller 101, determines whether the processing unit is to acquire the empty samples rack 104 or to let it pass through the connecting conveyance line.

After supply of empty samples racks 104 from the samples rack stopper 105, if all processing units have already acquired a necessary number of samples racks, part of those empty samples racks 104 may not be acquired by any processing unit. Empty samples racks 104 that have not been acquired are stocked on the empty-rack conveyance line 103 by means of the samples rack stopper 105 once again.

Figure 5:
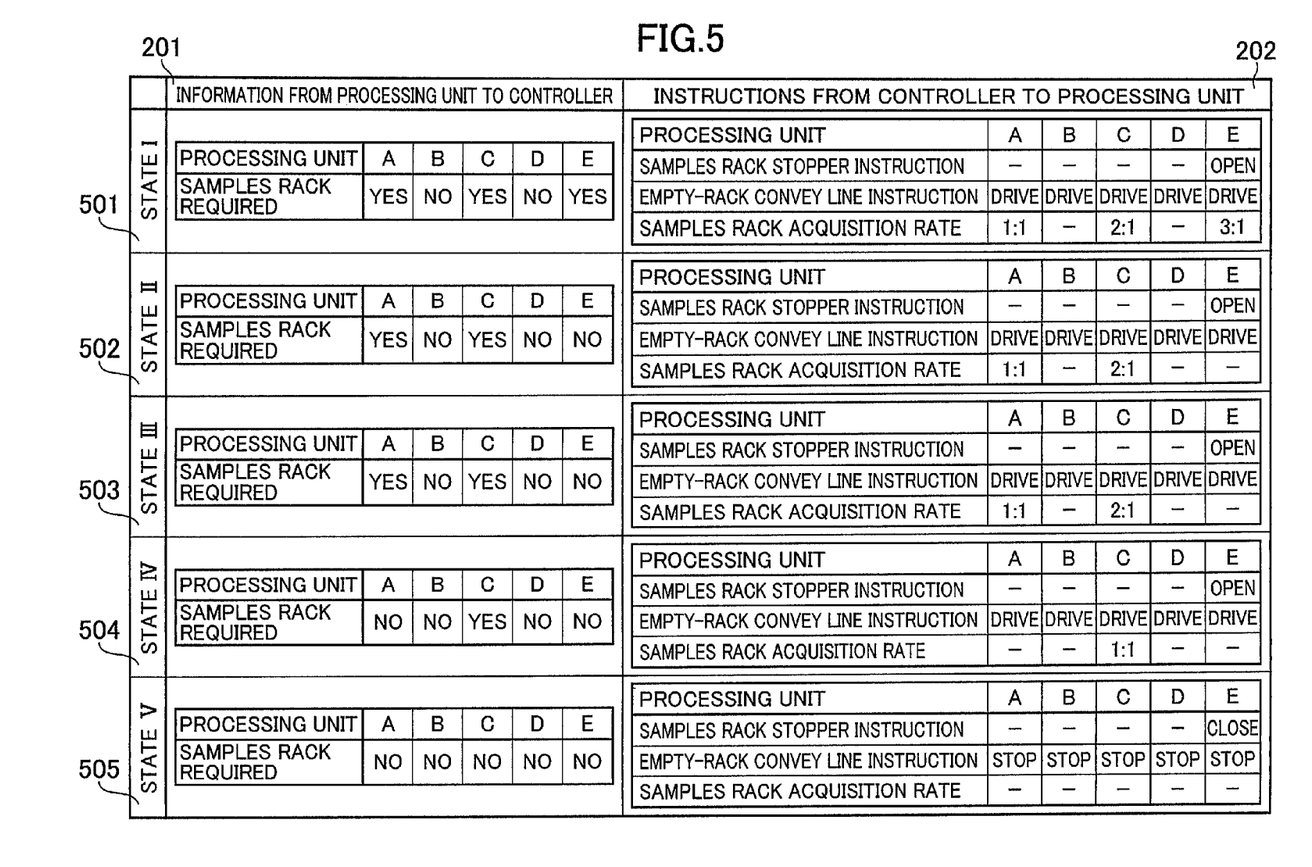
FIG. 5 shows an example of changes in a state of the information exchanged between the controller and processing units according to the present invention.

An example of changes in a state of the information exchanged between the processing units and the controller according to the present invention is shown in FIG. 5 with reference being made to the system configuration diagram of FIG. 1.

The following description assumes that: the processing unit A111 needs one empty samples rack 104, the processing unit C113 needs two empty samples racks 104, and the processing unit E115 needs one empty samples rack 104.

In the present invention, the samples rack acquisition rate is expressed as X:Y, which means that each processing unit is permitted to acquire a Y-number of empty samples racks 104 of all the X-number of empty samples racks that have arrived. In addition, the value of X is the number of processing units which have requested to the controller 101 to supply an empty samples rack 104. For example, if an N-number of processing units have requested the supply of an empty samples rack 104, an value of X=N and a samples rack acquisition rate of N:1 are displayed for the first processing unit that will be subjected to the conveyance of an empty samples rack from the samples rack stopper 105. A samples rack acquisition rate for a processing unit existing at a downstream position that is immediately next to the above processing unit and being in need of supply of an empty samples rack will be specified as either of N-1:1, N-2:1, etc., down to 1:1, depending upon an order in which conveyed empty samples racks arrive.

For instance, in the above example, the processing units A111, C113, E115 are each calling for a supply of an empty samples rack. The samples rack acquisition rate for the processing unit E will be specified as 3:1 since three processing units are calling for a supply of an empty samples rack and since the processing unit E115 is positioned at where the earliest of the conveyed empty samples rack will arrive.

Next empty samples rack will arrive at the processing unit D114. A samples rack acquisition rate, however, will not be specified since the processing unit D114 is not in need of supply of an empty samples rack.

Next empty samples rack will arrive at the processing unit C113. The controller 101 will therefore specify a samples rack acquisition rate of 2:1 to the processing unit C113.

Next empty samples rack will arrive at the processing unit B112. A samples rack acquisition rate, however, will not be specified for the same reason as for the processing unit D114.

Next empty samples rack will arrive at the processing unit A111. The controller 101 will specify a samples rack acquisition rate of 1:1 to the processing unit A111.

Under state I, the processing units A111, C113, E115 have reported to the controller 101 that each needs a supply of an empty samples rack 104. In response to this report, the controller 101 instructs the processing unit E115 to open the samples rack stopper 105 and the processing units A111 to E115 to drive the empty-rack conveyance line 103, thereby starting to supply an empty samples rack 104. The controller 101 also specifies samples rack acquisition rates to the processing units A111, C113, E115.

As a result, the processing unit E115 acquires the empty samples rack 104 that has been supplied from the samples rack stopper 105.

The conveyance of one empty samples rack 104 to the processing unit E115 was done in state-I 501, so the processing unit E115 no longer needs an empty samples rack 104 in state-II 502. An empty samples rack 104 is not yet supplied to the processing units A111 and C113 of the three units which have reported to the controller 101 the need to receive a supply of an empty samples rack. Once again, therefore, the controller 101 specifies the respective samples rack acquisition rates as 1:1 and 2:1 to the processing units A111 and C113.

The controller 101 instructs the processing unit E115 to open the samples rack stopper 105 and the processing units A111 to E115 to drive the empty-rack conveyance line 103. As a result, the processing unit C113 acquires one empty samples rack 104 supplied from the samples rack stopper 105.

One empty samples rack 104 was supplied to the processing unit C113 in state-II 502, but since the processing unit C113 is in need of two empty samples racks 104, the processing unit C113 is still in need of an empty samples rack in state-III 503. In addition, since an empty samples rack is not yet supplied to the processing unit A111, the information that was sent from this processing unit to the controller 101 to report that the unit needs an empty samples rack 104 still remains valid. The controller 101, therefore, specifies the samples rack acquisition rates as 1:1, 2:1 to the processing units A111, C113, respectively.

The controller 101 instructs the processing unit E115 to open the samples rack stopper 105 and the processing units A111 to E115 to drive the empty-rack conveyance line 103. Thus, one empty samples rack is conveyed. Under a situation of 2:1 having been specified, however, the processing unit C113 has acquired one samples rack that was conveyed above, and hence the unit C113 cannot acquire the samples rack that was supplied in state-III 503. The processing unit A111, therefore, acquires the samples rack.

Under state-IV 504, since an empty samples rack 104 was conveyed to the processing unit A111 in state III, the processing unit A111 no longer needs an empty samples rack 104, so only the information that was sent from the processing unit C113 to the controller 101 to report that the unit needs an empty samples rack 104 remains valid. Accordingly, the samples rack acquisition rate of 1:1 is specified to the processing unit C113.

The controller 101 instructs the processing unit E115 to open the samples rack stopper 105 and the processing units A111 to E115 to drive the empty-rack conveyance line 103. Hence, the processing unit C113 acquires an empty samples rack 104 supplied from the samples rack stopper 105.

Under state-V 505, since the processing units A111 to E115 no longer need an empty samples rack 104, the processing units A111 to E115 report to the controller 101 that the units do not need an empty samples rack 104. In response to this report, the controller 101 instructs the processing unit E115 to close the samples rack stopper 105 and the processing units A111 to E115 to stop the empty-rack conveyance line 103. Accordingly, the processing unit E115 closes the samples rack stopper 105 and the processing units A111 to E115 stop the empty-rack conveyance line 103.

Even in a system with a plurality of interconnected processing units, adopting the scheme of the present invention prevents uneven supply of samples racks and hence causes no process interruptions due to a shortage of samples racks. In addition, only the information indicating whether the processing unit is in need of empty samples racks is supplied from each processing unit to the controller 101, for which reason, supply of empty samples racks can be leveled without exchanging complex information.

Because of no need to exchange complex information, the system can also flexibly accommodate any changes in state that occur while the empty samples racks 104 that have been supplied from the samples rack stopper 105 arrive at the processing units. For example, in a case that the processing unit C113 removes samples from a samples rack 104, the samples rack 104 that has been emptied by the removal of the samples is conveyed from the main conveyance line 106 to the empty-rack conveyance line 103 via the connecting conveyance line 107, but the processing unit A111 can acquire the emptied samples rack 104 before empty samples racks are stocked in the samples rack stock section extending to the samples rack stopper 105. At this time, empty samples racks that are supplied from the samples rack stock section and become an excess because of a difference in time will be once again stocked on the empty-rack conveyance line 103 by the samples rack stopper 105 without being acquired by any processing units.

Figure 7:
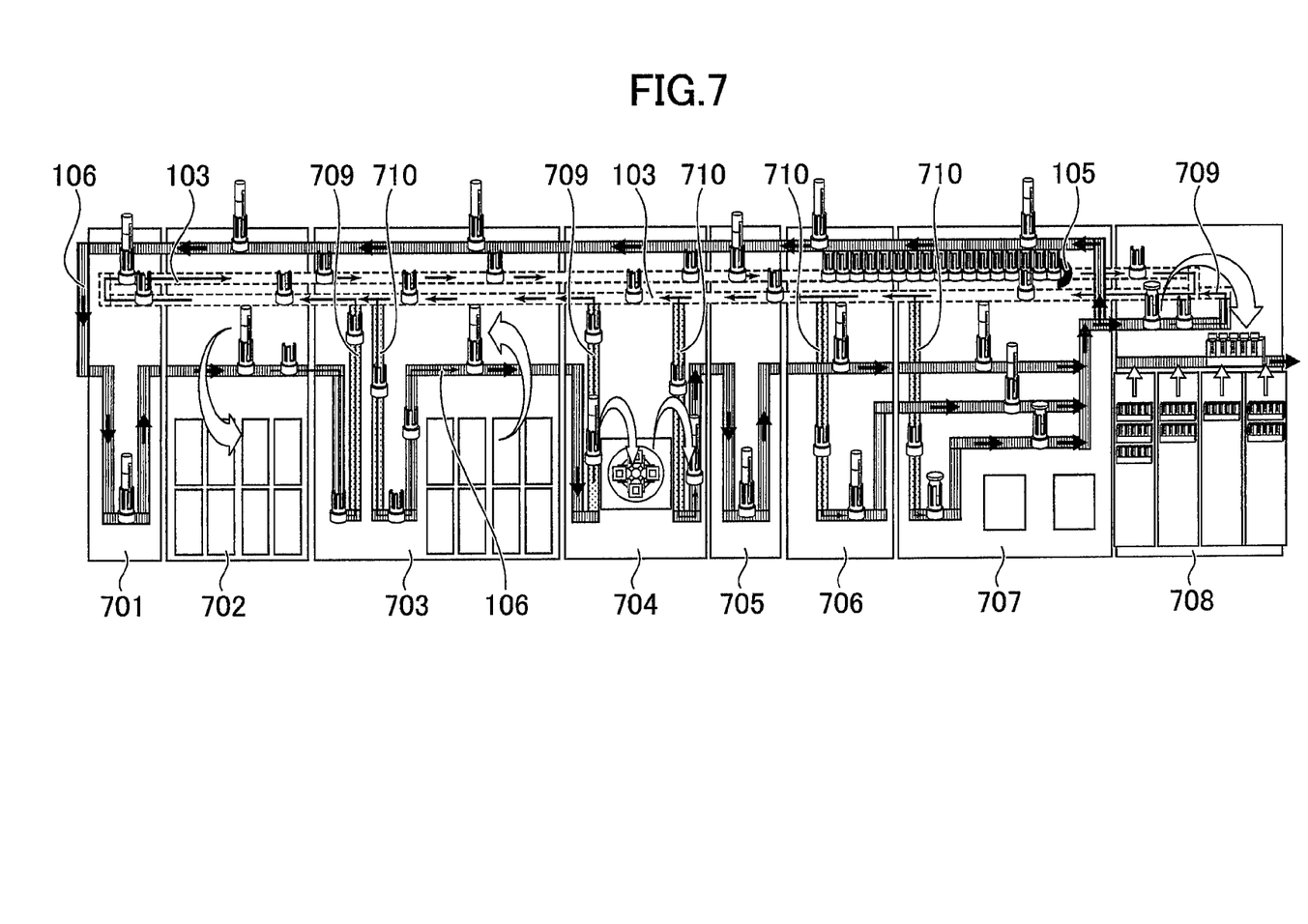
FIG. 7 shows an example of a processing unit configuration in the present invention.

FIG. 7 shows an example of a configuration in which only predetermined functions are assigned to the processing units in the automated sample test system. As shown in FIG. 7, from left, a stoppering unit 701, a storage unit 702, a loading unit 703, a centrifuging unit 704, a destoppering unit 705, a bar-code labeling unit 706, an aliquoting unit 707, and a transfer unit 708 are connected in series in the present embodiment. The automated sample test system in the present invention is not limited to the configuration shown in FIG. 7. The system configuration may include a smaller number of types of units than in FIG. 7, or may have units each connected to include nested or ramified branches.

The functions of each processing unit are described below.

After a plurality of samples have been stored into a loading tray and loaded by the operator, the loading unit 703 moves each sample from the loading tray into a samples rack via a samples chuck mechanism. The loading unit 703 also reads information from the sample and logically binds the information thereto for indicating in what samples rack the sample has been mounted.

The centrifuging unit 704 centrifuges a sample.

The destoppering unit 705 removes a stopper of a test tube which is a samples container.

The bar-code labeling unit 706 provides test tubes for accommodating a sample that has been divided into smaller quantities, and affixes bar-code labels to the test tubes.

The aliquoting unit 707 provides samples cups for accommodating a sample that has been divided into smaller quantities, and dispenses the sample in quantitatively subdivided form into the samples cups. Alternatively, the aliquoting unit 707 dispenses the sample in quantitatively subdivided form into the test tubes provided by the bar-code labeling unit 706.

The transfer unit 708 classifies child samples or parent samples that have been subjected to processing in the automated sample test system, and then moves the system-processed samples to samples racks appropriate for an analyzer which is to analyze the samples. In the present embodiment, the samples are moved from one-sample placement racks to five-sample placement racks.

The stoppering unit 701 mounts the stopper of a test tube, a samples container.

The storage unit 702 moves the samples from a samples rack to the loading tray via the samples chuck mechanism.

The main conveyance line 106 that conveys the samples from the samples rack to the processing units is disposed in such a form as to extend along each processing unit. Additionally, the empty-rack conveyance line 103 that conveys empty samples racks is disposed at a lower section of the processing unit. The connecting conveyance line 710 is provided to exchange empty samples racks between the empty-rack conveyance line and the main conveyance line or between the empty-rack conveyance line and the processing unit. On the empty-rack conveyance line, the samples rack stopper 105 that stems movements of empty samples racks is disposed and a plurality of samples racks whose movements have been stemmed by the stopper are standing by.

Operation of each processing unit, empty-rack conveyance line, main conveyance line, and connecting conveyance line, is controlled by a controller not shown.

In the exemplary configuration diagram of FIG. 7, the processing units that require supply of empty racks are the loading unit 703, the centrifuging unit 704, the bar-code labeling unit 706, and the aliquoting unit 707.

Empty rack consumption differs between the processing units according to particular characteristics of the processing unit. For example, the loading unit 703 and the centrifuging unit 704 consume empty racks according to the number of parent samples loaded from the outside, whereas the bar-code labeling unit 706 and the aliquoting unit 707 consume empty racks according to the number of requested test items (child samples). In general, since a plurality of analytical items are requested for one parent sample, a bar-code labeling unit and an aliquoting unit require more empty racks than a loading unit and a centrifuging unit do. Therefore, the connecting conveyance line 710 that efficiently supplies empty racks from the empty-rack conveyance line 103 to the main conveyance line 106 in order to implement efficient supply of empty racks to the processing units may be provided only at the processing units.

The storage unit 702, the centrifuging unit 704, and the transfer unit 708, on the other hand, remove samples from each samples rack, thereby generating empty racks. To avoid congestion of a multitude of empty samples racks on the main conveyance line, therefore, the connecting conveyance line 709 that collects empty racks from the main conveyance line 106 onto the empty-rack conveyance line 103 may be provided only at the loading unit 703, the centrifuging unit 704, and the transfer unit 708. This layout, allowing for connecting a plurality of storage units 702, serves as a measure to eliminate a need to provide an independent connecting conveyance lines (empty-rack recovery lines) 709 at each storage unit 702. In this case, the connecting conveyance lines (empty-rack recovery lines) may be provided at adjacent loading units 703, not the storage units 702.

In the present embodiment, description of a time required for each processing unit to consume an empty samples rack 104 is omitted and Y in samples rack acquisition rate X:Y is fixed at 1. If the processing units differ in empty-rack consumption, however, changing the value of Y allows a processing unit larger in empty-rack consumption to preferentially acquire the empty samples rack 104.

DESCRIPTION OF REFERENCE NUMBERS

101 Controller
102 Communication cable
103 Conveyance line for empty racks
104 Samples rack
105 Samples rack stopper
106 Main conveyance line
107 Connecting conveyance line
108 Samples existence detection sensor
111 Processing unit A
112 Processing unit B
113 Processing unit C
114 Processing unit D
115 Processing unit E
201 Report from processing unit to controller
202 Instruction from controller to processing unit
301 Empty-rack supply determining step
302 Empty-rack conveyance line driving instruction step
303 Samples rack acquisition rate determining step
304 Samples rack stopper existence determining step
305 Samples rack stopper opening instruction step
306, 310 End-of-instruction determining step
307 Empty-rack conveyance line deactivation instruction step
308 Samples rack stopper existence determining step
309 Samples rack stopper closing instruction step
401 Samples rack stopper opening/closing step
402 Empty-rack conveyance line driving instruction step
403 Empty-rack request existence determining step
404 Empty-rack arrival awaiting step
405 Samples rack acquisition determining step
406 Empty-rack acquisition step
407 Empty-rack pass-through step
501 State I
502 State II
503 State III
504 State IV 505 State V
601 Error source marker
602 Operational status display area
603 Error message display area
701 Stoppering unit
702 Storage unit
703 Loading unit
704 Centrifuging unit
705 Destoppering unit
706 Bar-code labeling unit
707 Aliquoting unit
708 Transfer unit
709 Connecting conveyance line (for recovering empty racks)
710 Connecting conveyance line (for supplying empty racks)

The invention claimed is:

1. An automated sample test system, comprising:
processing units that each process samples conveyed after being placed in samples racks;
an empty-rack stock line on which are stocked the samples racks not holding a sample;
communication means that collects information on whether the processing units require empty samples racks; and
a controller which, on the basis of information obtained via the communication means, controls the processing units to acquire empty samples racks at a predetermined rate of all those supplied from the empty-rack stock line to the processing units.

2. The automated sample test system according to claim 1, further comprising:
a samples existence sensor that detects whether samples are placed on a samples rack; and
notifying means which, upon the samples existence sensor detecting completion of conveyance of samples-containing samples racks present on the empty-rack stock line, notifies the completion to an operator.

3. The automated sample test system according to claim 1, wherein
the empty-rack stock line is provided at a lower position than the samples conveyance line.

4. The automated sample test system according to claim 1, further comprising:
a connecting conveyance line that conveys empty samples racks between the empty-rack stock line and the processing units.

5. The automated sample test system according to claim 4, wherein the connecting conveyance line includes:
a supply line for supplying empty samples racks from the empty-rack stock line to the samples conveyance line or the processing units; and
a recovery line for collecting empty samples racks from the samples conveyance line or the processing units onto the empty-rack stock line.

6. The automated sample test system according to claim 5, wherein:
the processing units include at least one of a bar-code labeling unit and an aliquoting unit; and
the supply line supplies empty samples racks to the at least one of the bar-code labeling unit and the aliquoting unit.

7. The automated sample test system according to claim 5, wherein:
the processing units include at least one of a storage unit, a centrifuging unit, and a transfer unit; and
the recovery line recovers empty samples racks from at least one of the storage unit, the centrifuging unit, and the transfer unit.

8. The automated sample test system according to claim 1, wherein:
the empty-rack stock line includes an empty-rack conveyance line for conveying empty samples racks, and at least one rack stopper for holding empty samples racks at a predetermined position on the empty-rack conveyance line; and
the controller is configured to open or close the rack stopper, depending upon the information.

9. The method for controlling an automated sample test system according to claim 8, further comprising:
deactivating the empty-rack conveyance line when none of the processing units requires supply of an empty samples rack.

10. The automated sample test system according to claim 1, wherein the controller is configured to compare both a number of empty samples racks already arrived at the processing unit and a number of empty samples racks already acquired by the processing unit with the samples rack acquisition rate, upon an arrival of an empty samples rack at a processing unit,
wherein the controller is configured to acquire the new arrival of an empty samples rack, when the ratio of the number of empty samples racks already arrived at the processing unit and the number of empty samples racks already acquired by the processing unit agree with the samples rack acquisition rate,
wherein the controller is configured to convey the new arrival of one or more empty samples racks to other processing units to which empty samples racks are to be conveyed subsequent to the processing unit, when the ratio of the number of empty samples racks already arrived at the processing unit and the number of empty samples racks already acquired by the processing unit disagree with the samples rack acquisition rate.

11. The automated sample test system according to claim 10,
further comprising an empty-rack stock section for stocking empty samples racks,
wherein the controller is configured to store the empty samples racks into the empty-rack stock section, when none of the processing units acquires the conveyed empty samples rack.

* * * * *